United States Patent [19]

Forster

[11] 4,196,517
[45] Apr. 8, 1980

[54] ORTHODONTIC BRACKET

[75] Inventor: Rolf Förster, Pforzheim, Fed. Rep. of Germany

[73] Assignee: Firma Bernhard Forster, Pforzheim, Fed. Rep. of Germany

[21] Appl. No.: 921,188

[22] Filed: Jul. 3, 1978

[30] Foreign Application Priority Data

Jul. 16, 1977 [DE] Fed. Rep. of Germany ... 7722333[U]

[51] Int. Cl.$^2$ .............................................. A61C 7/00
[52] U.S. Cl. ..................................................... 433/17
[58] Field of Search ........................................ 32/14 A

[56] References Cited

U.S. PATENT DOCUMENTS

| | | | |
|---|---|---|---|
| 2,104,192 | 1/1938 | Ford | 32/14 A |
| 3,084,437 | 4/1963 | Neger | 32/14 A |
| 3,238,619 | 3/1966 | Brunson et al. | 32/14 A |
| 4,077,126 | 3/1978 | Pletcher | 32/14 A |

Primary Examiner—Robert Peshock

[57] ABSTRACT

The bracket according to the invention includes the following structure:

Flange means provided for securing the bracket to the teeth of a patient. A bearing member having a through hole on an axis that is transversely spaced from the flange means. Connecting means connect the bearing member and the flange means and have a neck portion. A rotary catch is mounted in the bearing member for rotation on said axis and defines with said neck portion and the flange means a channel, which is disposed on one side of the bearing member and open opposite to the neck portion and adapted to receive a wire so that the latter is engageable with the neck portion. The rotary catch channel is rotatable about the axis to and from a wire-retaining position and in the wire-retaining position is adapted to retain a wire in the channel.

12 Claims, 5 Drawing Figures

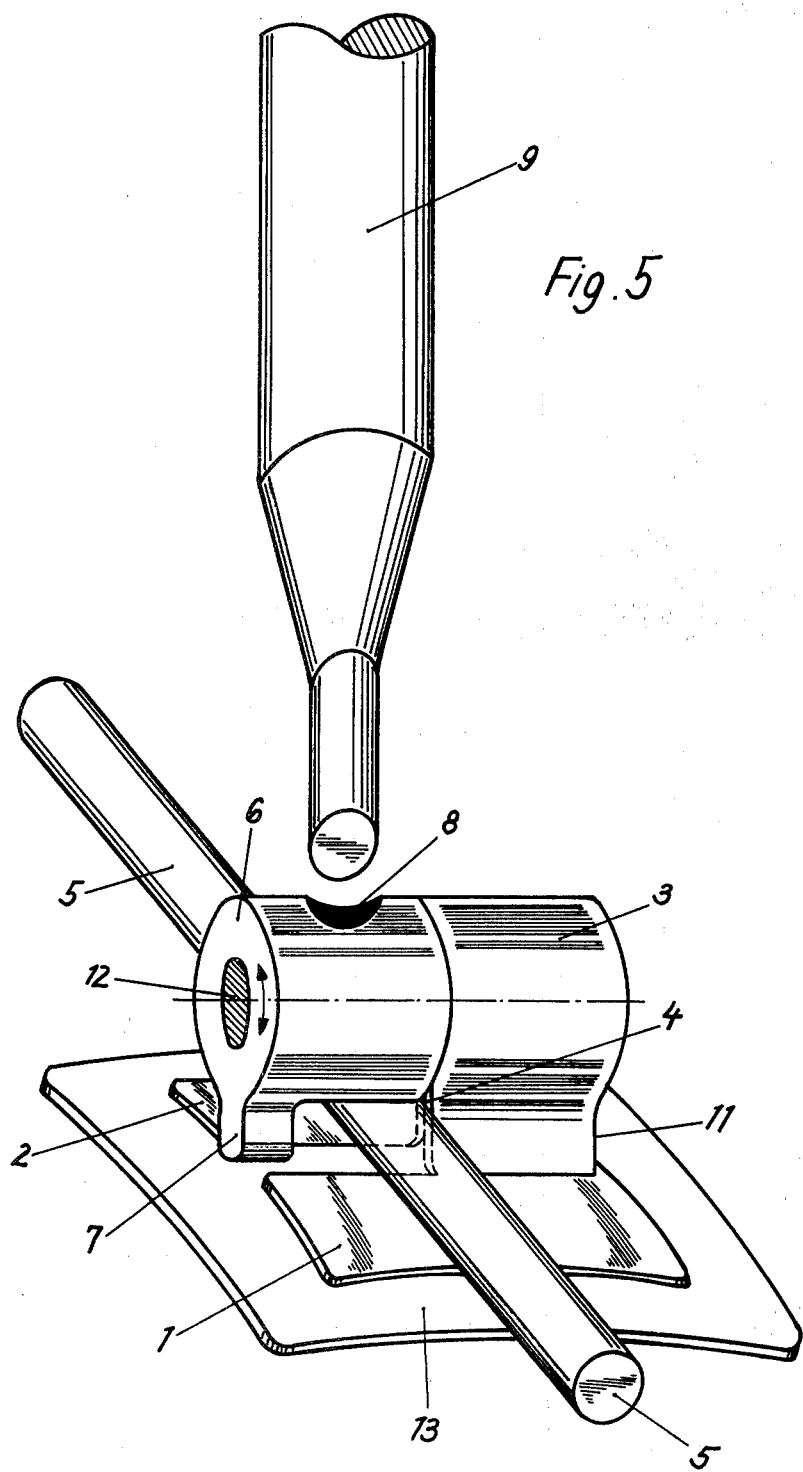

ORTHODONTIC BRACKET

This invention relates to an orthodontic bracket, which is engageable by a tensioned wire used to correct a tooth and is adapted to be secured to a tooth to be corrected by the action of said tensioned wire or to a tooth to which said tensioned wire is to be anchored.

It is known to use orthodontic brackets consisting of small plates, which are cemented to a tooth and provided with hooks for receiving tensioned wires, which must be connected to the hooks by means of wire loops or the like. This is difficult and cannot be effected satisfactorily in all positions in the patient's mouth.

It is an object of the invention to provide brackets to which the tensioned wires can easily and reliably be connected.

In accordance with the invention, an orthodontic bracket for connection to a tensioned wire comprises two flat flanges, which are adapted to be cemented or welded, a bearing member, which is disposed between the flanges and connected thereto by a wire-engageable neck portion, and a rotary catch, which is rotatably mounted in the bearing member and with the neck portion and the flange plates defines a channel, which is open on the side opposite to the neck portion and adapted to be closed by the rotary catch.

Specifically, the rotary catch may be mounted in the bearing member for rotation on an axis which is transversely spaced from and parallel to the plane in which the flange plates extend and has a radially protruding catch nose, which is axially spaced from the bearing member. On that side of the bearing member which is opposite to the catch nose, a disc spring may be provided which urges the rotary catch into frictional engagement with the bearing member.

The neck portion may be connected to the two flange plates by a cross-piece, which is formed with an axial groove for receiving a tooth-erecting spring. The rotary catch may have through bores for receiving tooth-erecting springs. The rotary catch is provided diametrically opposite to its nose with a blind bore for adjusting the rotary catch.

An advantageous embodiment of the bracket according to the invention will be described hereinafter by way of example with reference to the drawing, in which FIGS. 1 and 2 are a top plan view and a side elevation showing the bearing member of the bracket, without and with a rotary catch.

FIG. 5 is a perspective view showing the bracket mounted on a mounting strap and represented in a position assumed during the actuation of the bracket.

Figure 1:
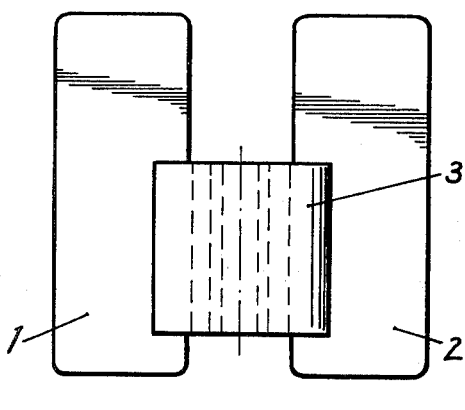

As is apparent from the drawing, the orthodontic bracket comprises two flange plates 1, 2, which extend generally in a plane and a bearing member 3, which is provided with a bearing 3a having an axis which is transversely spaced from and parallel to the plane of the flange plates 1, 2 extend. The latter are disposed on opposite sides of a normal projection of the axis of the bearing 3a on the plane of the flange plates. The flange plates 1, 2 may be fixed by cementing or welding. The bearing member 3 is connected to the flange plates 1, 2 by a neck portion 4, which is engageable by a wire 5. A rotary catch 6 is provided with a pivot pin 6a, which is mounted in the bearing 3a so that the rotary catch 3 is rotatable on the axis of the bearing 3a. The rotary catch 6 carries a laterally protruding catch nose 7, which is axially spaced from the bearing member 3 on one side thereof.

Figure 2:
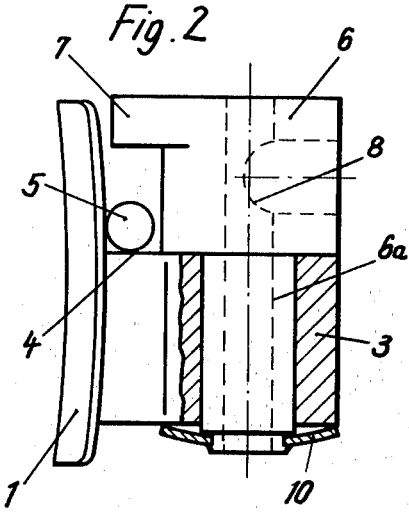
Figure 3:
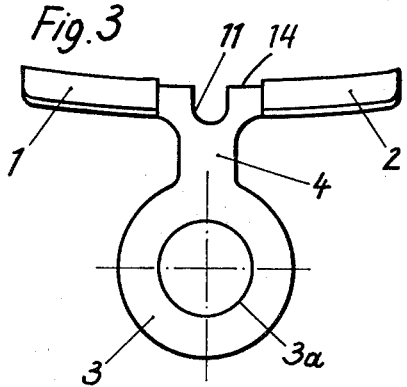
FIGS. 3 and 4 are front elevations showing the bearing member without and with a rotary catch, respectively.

When viewed in cross-section as shown in FIG. 2, the flange plates 1, 2, the neck portion 4, and the rotary catch 6 define a channel, which is disposed on one side of the bearing member 3 and open opposite to the neck portion 4.

Diametrically opposite to the catch nose 7, which faces the channel, the rotary catch is provided with a blind bore 8 for receiving an end pin of an implement 9, which can be used to move the rotary catch 6 between a position in which the catch nose 7 is clear of the channel defined by the flange plates 1, 2, the neck portion 4, and the rotary catch 6, and a wire-retaining position in which the catch nose closes the channel opposite to the neck portion 4. This is apparent from FIGS. 4 and 5.

Figure 4:
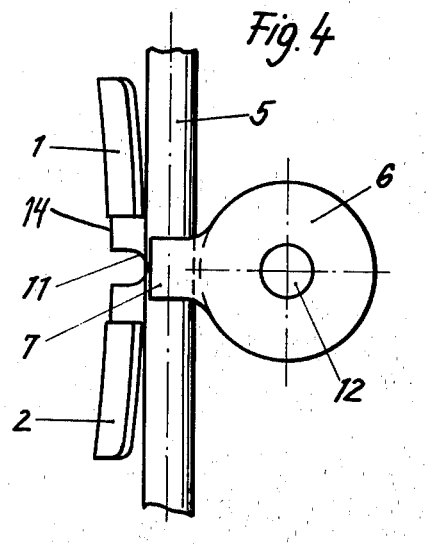

On the side of the bearing member 3 which is opposite to the catch nose 7, the flange plates 1, 2, the neck portion 4, and the rotary catch 6 define a channel when viewed in cross-section as shown in FIG. 2. The rotary catch 6 is pivoted on an axis which is transversely spaced from and parallel to the plane of the flange plates 1, 2. The rotary catch 6 is pivotally movable to a position in which the catch nose 7 overlies the gap between the plates 1, 2, as is shown in FIGS. 4, 5. A disc spring 10 is provided and urges the rotary catch 6 into frictional engagement with the bearing member 3. This is apparent from FIG. 2.

The neck portion 4 is connected to the two flange plates 1, 2 by a cross-piece 14, which is formed with an axial groove 11. Tooth-erecting springs not shown, can be fitted in said groove. The rotary catch 6 has a through bore 12, which can also receive tooth-erecting springs so that the field of application of the bracket is enlarged. The flange plates 1, 2 may be directly cemented to the tooth to be corrected or may be secured to the tooth by means of a strap 13 to which the bracket is secured.

In the embodiment which has just been described, the bracket is intended to be applied to a tooth which is to be corrected by a force exerted by a tensioned wire 5 which is in slidable engagement with the neck portion 4 in the channel defined by the neck portion with the flange plates 1, 2 and the rotary catch 6 and is retained in the channel by the catch nose 7 which closes the channel opposite to the neck portion 4.

Modified brackets may be used to secure the tensioned wire to teeth which are disposed on opposite sides of the tooth. In such modified brackets, the rotary catch is adapted in its wire-retaining position to clamp the wire 5 against the flange plates 1, 2.

What is claimed is:

1. An orthodontic bracket, comprising
   flange means, for securing the bracket to a tooth of a patient,
   a bearing member having a through hole on an axis that is transversely spaced from said flange means,
   connecting means which connect said bearing member and said flange means, said bearing member being provided with a neck portion engaging said connecting means,
   a rotary catch member mounted in said bearing member for rotation on said axis, and defining with said neck portion and said flange means a channel, which is disposed on one side of said bearing member and open opposite to said neck portion and adapted to receive a wire so that the latter is engageable with said neck portion, said rotary catch being formed with a radial blind bore which is peripherally spaced from the side of said rotary catch facing said channel, and engageable by an implement for rotating said catch, and said rotary catch being rotatable on said axis to a wire-retaining position and in said wire-retaining position being adapted to retain a wire in said channel.

2. An orthodontic bracket as set forth in claim 1, in which said rotary catch has a laterally protruding nose, which is axially spaced from said bearing member, and said rotary catch is rotatable on said axis between a position in which said nose is clear of said channel and a wire-retaining position in which said nose closes said channel opposite to said neck portion.

3. An orthodontic bracket as set forth in claim 2, in which said blind bore is diametrically opposite to said nose.

4. An orthodontic bracket as set forth in claim 1, in which said flange means extend in a plane on opposite sides of a normal projection of said axis on said plane.

5. An orthodontic bracket as set forth in claim 1, in which said flange means comprise two flange plates, which are laterally spaced apart in a plane.

6. An orthodontic bracket as set forth in claim 5, in which said flange plates are disposed on opposite sides of a normal projection of said axis on said plane.

7. An orthodontic bracket as set forth in claim 5, in which said axis is parallel to said plane and said connecting means comprise a crosspiece which is joined to both said flange plates and to said neck portion and formed on the side opposite to said neck portion with a groove which is parallel to said axis.

8. An orthodontic bracket as set forth in claim 4, in which said axis is parallel to said plane.

9. An orthodontic bracket as set forth in claim 1, in which said rotary catch extends through said through hole to the side of said bearing member which is opposite to said channel and a disc spring is disposed between said bearing member and said rotary catch on the side opposite to said channel and urges said catch into frictional engagement with said bearing member.

10. An orthodontic bracket as set forth in claim 1, in which said rotary catch has at least one through bore.

11. An orthodontic bracket as set forth in claim 10, in which said through bore of said rotary catch is parallel to said axis.

12. An orthodontic bracket as set forth in claim 1, in which said rotary catch is adapted to clamp a wire in said channel against said flange means when said rotary catch is in said wire-retaining position.

* * * * *